United States Patent [19]
Müller et al.

[11] 3,996,014
[45] Dec. 7, 1976

[54] METHANATION REACTOR

[75] Inventors: Wolf-Dieter Müller, Frankfurt am Main; Friedrich-Wilhelm Möller, Seulberg; Karl Pirl, Bad Nauheim-Rodgen, all of Germany

[73] Assignee: Metallgesellschaft Aktiengesellschaft, Frankfurt am Main, Germany

[22] Filed: June 4, 1975

[21] Appl. No.: 583,827

[30] Foreign Application Priority Data

June 7, 1974 Germany .......................... 2427530

[52] U.S. Cl. ............................................. 23/288 R
[51] Int. Cl.² ............................................. B01J 8/04
[58] Field of Search ........................ 23/288 R, 289; 48/61 US

[56] References Cited
UNITED STATES PATENTS

| | | | |
|---|---|---|---|
| 1,682,787 | 9/1928 | Jaeger | 23/288 R |
| 2,363,738 | 11/1944 | Mather et al. | 23/288 R |
| 2,475,855 | 7/1949 | Peters | 23/288 R |
| 2,512,562 | 6/1950 | Cummings | 23/288 R |
| 2,722,501 | 11/1955 | Kassel | 23/288 R UX |
| 2,969,318 | 1/1961 | Woodall, Jr. | 23/288 R X |
| 3,249,405 | 5/1966 | Waddill | 23/288 R |
| 3,433,609 | 3/1969 | Percival et al. | 23/288 R X |
| 3,477,833 | 11/1969 | McMullin et al. | 23/288 R X |
| 3,609,097 | 9/1971 | Koppe | 23/288 R X |
| 3,754,078 | 8/1973 | Hinrichs et al. | 23/289 X |

*Primary Examiner*—Joseph Scovronek
*Attorney, Agent, or Firm*—Burgess, Dinklage & Sprung

[57] ABSTRACT

A reactor for catalytically converting gases containing carbon oxides, hydrogen and water vapor into methane under elevated temperatures and pressures. The reactor includes a substantially cylindrical outer shell which is provided at opposite end faces with a gas inlet and a gas outlet. An inner vessel contains part of the catalyst volume for the reactor which is impermeable to gas adjacent to the gas inlet. The inner vessel has a substantially cylindrical shell which defines a flow passage with the inner surface of the outer shell of the reactor and has openings for the radially inward passage of the gas mixture to be reacted. A perforated central gas-collecting tube containing no catalyst is positioned in the inner vessel and one or preferably two additional catalyst beds are positioned between the inner vessel and the gas outlet.

2 Claims, 1 Drawing Figure

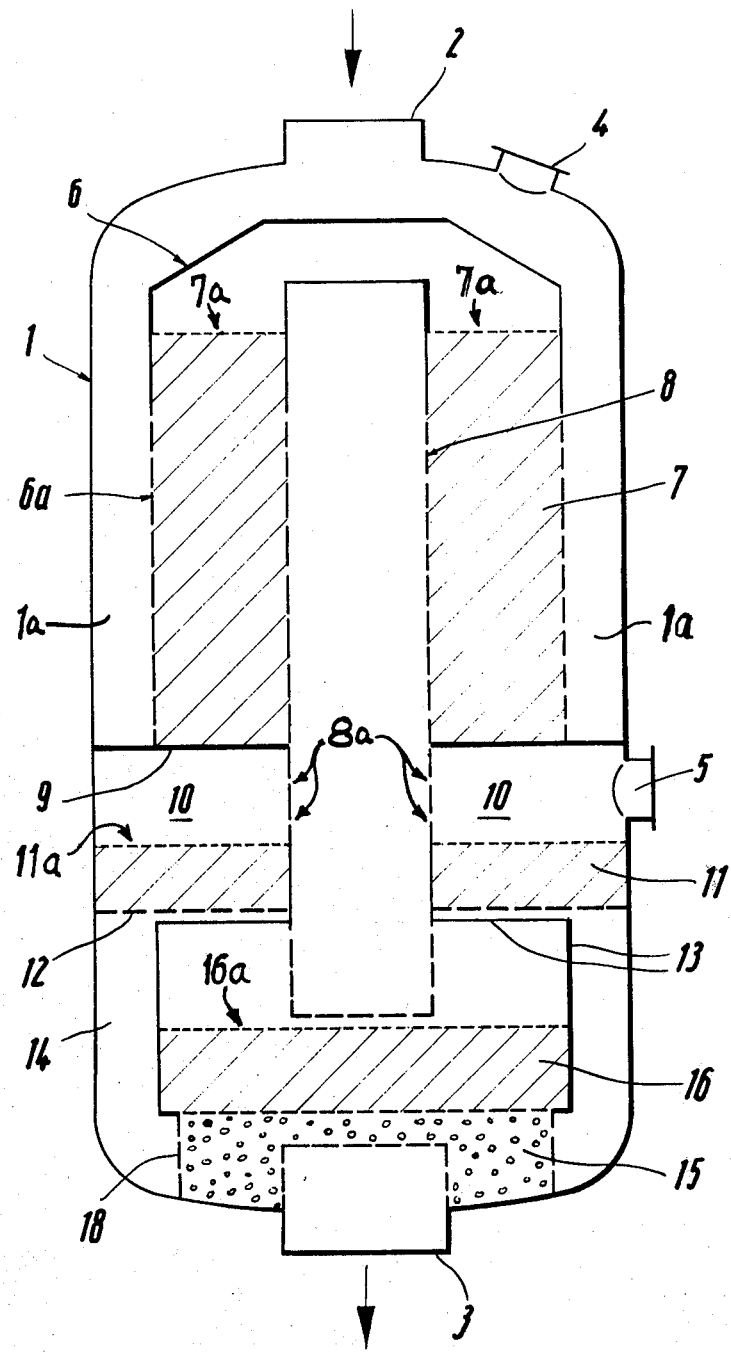

METHANATION REACTOR

BACKGROUND

This invention relates to a reactor for catalytically converting gases which contain carbon oxides, hydrogen and water vapor into methane at temperatures between about 250° C and 550° C and under pressures in the range of 10–80 kg/cm², comprising a substantially cylindrical outer shell, which is provided at opposite end faces with a gas inlet and a gas outlet.

A catalytic methanation stage is often included in a process of producing high-methane gases, such as synthetic natural gas. In a preceding process step, a rich gas is produced, which consists mainly of methane and contains also carbon monoxide, carbon dioxide, and hydrogen. The gas mixture to be methanated contains in most cases also water vapor in the amount required for methanation.

The reactor according to the invention is intended for such methanation, which is carried out in most cases with the aid of nickel-containing catalysts, which contain 30–60% by weight nickel on a support. Supports of various kinds, such as alumina, magnesium silicate or magnesium spinel, may be used for this purpose. The catalytic reaction of carbon oxides and hydrogen is an exothermic reaction. For this reason, known methanation reactors comprise a plurality of superimposed catalyst beds, which are cooled with water. Shaft reactors are also known, in which the gas mixture to be reacted flows through a single, uninterrupted catalyst bed.

In connection with a methanation reactor which is large in volume and in excess of 3 m in diameter, special problems arise because such reactors can be transported only with very great difficulty or must be erected directly on the site of the gas-producing plant. Another difficulty resides in the differential thermal expansion of the top and bottom portions of the reactor as a result of the exothermic nature of the reaction. This differential thermal expansion gives rise to different shear stresses in the reactor, particularly in its outer shell.

SUMMARY

This invention provides a reactor which can be manufactured at low cost and in which thermal stresses are eliminated as far as possible. This is accomplished according to the invention in that part of the catalyst volume is contained in an inner vessel which is impermeable to gas adjacent to the inlet and has a substantially cylindrical shell, which defines a flow passage with the inside surface of the outer shell of the reactor and has openings for the passage of the gas mixture to be reacted. The gas flows substantially radially inwardly through the catalyst in the inner vessel. As a result, the gas mixture, which enters the reactor at a relatively low temperature of about 250°–350° C can first fill the space between the inside surface of the outer shell and the inner vessel before the gas contacts the catalyst and the exothermic methanation begins. Because the outer shell of the reactor is thus shielded from high temperatures, the outer shell can be designed for a lower temperature so that the manufacturing costs are greatly reduced.

DESCRIPTION

To minimize the pressure loss to which the gas to be reacted is subjected as it flows through the catalyst, a perforated central gas-collecting tube which contains no catalyst is contained in the inner vessel. That tube collects the gas when it has reacted to a high degree and the gas then flows in said tube to the gas outlet of the reactor without a further pressure loss.

At least one additional catalyst bed is suitably arranged between the inner vessel and the gas outlet and serves further to improve the degree of conversion of the gas mixture. This additional catalyst bed or beds has or have a low height so that this bed or these layers do not result in a substantial additional pressure loss. In practice, the volume of the catalyst contained in the vessel amounts to about 60–90%, preferably 75–85%, of the entire catalyst volume and the remainder is contained in the additional bed or beds.

An embodiment of the reactor according to the invention will now be explained by way of example with reference to the drawing, which is a longitudinal vertical sectional view showing the reactor.

The reactor has a substantially cylindrical outer shell 1, which is provided with a gas inlet opening 2 and a gas outlet opening 3 at its top and bottom end faces, respectively. For maintenance work and the like, a person can enter the interior of the reactor through manholes 4 and 5, which are tightly closed by covers during operation. An inner vessel 6 which contains catalyst 7 is contained in the upper portion of the reactor. The vessel 6 contains a central gas-collecting tube 8, which extends downwardly through the bottom 9 of the vessel 6. Bottom 9 is impermeable to gas, this bottom extends between shell 1 and tube 8 and supports catalyst 7.

The inner vessel 6 is impermeable to gas in its upper portion, which is nearest to the gas inlet 2. The shell portion 6a of the inner vessel 6 has a large number of openings, which are indicated by dotted lines in the drawing. The upper end of the gas-collecting tube 8 is also impermeable to gas. The tube 8 is perforated also in its other portions contained in the vessel 6 in order to enable an ingress of gas.

The catalyst bed 7 extends upwardly beyond the perforated portions of the vessel 6 and of the tube 8. The gas-permeable upper surface of catalyst bed 7 is designated 7a. The gas coming from the annular chamber 1a between the shell 1 and the perforated portion 6a of inner vessel 6 is constrained to flow radially inwardly through catalyst 7. Annular chamber 1a is closed at its lower end by bottom 9. The diameter of the shell portion 6a is preferably about 0.85–0.97 times the inside diameter of the reactor shell 1 and the diameter of the gas-collecting tube 8 in this region is suitably 0.1–0.3 times the diameter of the outer shell. The volume of the catalyst material 7 is about 60–90%, preferably 75–85%, of the entire catalyst volume in the reactor.

The gas which has collected in the tube 8 flows downwardly and can enter the clearance space 10 through perforations 8a in the tube. From the clearance space 10 the gas must flow through a catalyst bed 11, with gas-permeable upper surface 11a. The catalyst bed 11 lies on a grate 12. The catalyst bed 11 extends from the tube 8 to the inside surface of the reactor shell 1. The tube 8 is impermeable to gas adjacent to this bed.

A gas-impermeable hood 13 extends from the tube 8 and the largest diameter of said hood 13 is smaller than the inside diameter of the shell 1. As a result, an annular flow passage 14 is left between the hood 13 and the shell 1. The gas coming from the catalyst bed 11 flows through this annular clearance 14 and finally through non-catalytic packing 15 to the gas outlet 3. The packing 15 consists, e.g., of ceramic balls, which have no catalytic activity and result only in a small pressure loss of the gas flowing through the packing. The hood 13 rests on a supporting rim 18 which is permeable to gas.

Any gas in the tube 8 which does not flow through the catalyst bed 11 will emerge at the perforated lower end of the tube 8 within the hood 13 and will then flow through a second catalyst bed 16 with a gas-permeable surface 16a. The second catalyst bed lies on the packing 15 and is confined at its periphery by the hood 13. This portion of the gas flows from the second catalyst bed 16 through the packing 15 and then through the gas outlet 3. The two catalyst beds 11 and 16 promote a reaction of gas portions which as a result of an unintended channeling in the catalyst 7 have flown through the latter without being reacted. The catalyst beds 11 and 16 have usually the same height. The height of each catalyst bed 11 or 16 is in most cases 0.1–0.25 times the diameter of the outer shell 1 of the reactor.

The arrangement shown on the drawing may be modified in that the catalyst bed 11 and the hood 13 are omitted and the catalyst bed 16 is designed to occupy the entire inside diameter of the reactor. In this case, only one protective bed is provided to promote a complete reaction of gas which has not yet reacted in the catalyst bed 7. A single catalyst bed 16 will usually comprise about 10–15% of the entire catalyst. The use of the two beds 11 and 16 shown in the drawing has the advantage that the gas volume leaving the tube 8 is divided into two parts so that the pressure loss in the catalyst bed is reduced. When all gas must flow through one bed, the gas will flow at a higher velocity so that the pressure loss in this bed will be four times the pressure loss in two beds having the same height. If the catalyst volume of the other bed is added, the pressure loss will be eight times the pressure loss in two beds.

The teachings of the invention afford special advantages in reactors which have an outer shell that is more than 3 m to about 5 m in diameter. In this case the length of the reactor is about 1.5–3.5 times its diameter.

A reactor of the kind shown on the drawing may have, e.g., the following dimensions:

| | |
|---|---|
| Diameter of outer shell 1 of the reactor | 3.8 m |
| Diameter of inner vessel 6 | 3.4 m |
| Diameter of gas-collecting tube 8 | 1 m |
| Height of catalyst bed 7 | 4 m |
| Height of each of catalyst beds 11 and 16 | 0.5 m |
| Length of reactor | 9.5 m |

What is claimed is:
1. A reactor for catalytically converting gases which contain carbon oxides, hydrogen and water vapor into methane at temperatures between about 250° C and 550° C and under pressures in the range of 10–80 kg/cm$^2$, comprising a substantially cylindrical outer shell provided at opposite end faces with a gas inlet and a gas outlet, an inner vessel impermeable to gas adjacent the inlet and having a substantially cylindrical shell which defines a flow passage with the inside surface of the outer shell of the reactor, said shell having openings for the radially inward passage of the gas mixture to be reacted, a central gas collecting tube containing no catalyst and positioned axially in the inner vessel, a catalyst occupying about 60–90% of the volume of the annulus of said inner vessel, said tube being perforated within said inner vessel, a bottom impermeable to gas positioned below said inner vessel and extending between said tube and said outer shell, a first horizontal catalyst bed below said bottom and supported by a grate, a clearance space between said first horizontal catalyst bed and said bottom, said tube extending through said clearance space and said first horizontal catalyst bed, said tube being perforated near said clearance space and being impermeable to gas within said first horizontal catalyst bed, a hood below said first horizontal catalyst bed extending from said tube downwardly to a second horizontal catalyst bed positioned within said hood near said gas outlet, said tube extending with its perforated end portion into said hood, at least one catalyst-free flow passage between said second horizontal catalyst bed and said inside surface of said outer shell and from the grate of said first horizontal catalyst bed to said gas outlet, whereby in order for gas from said tube to leave said reactor through said gas outlet it must flow either through said first horizontal catalyst bed or said second horizontal catalyst bed.

2. The reactor of claim 1, including a non-catalytic packing supporting said second horizontal catalyst bed.

\* \* \* \* \*